US00PP08775P

United States Patent [19]

McRae

[11] Patent Number: Plant 8,775

[45] Date of Patent: Jun. 7, 1994

[54] LILY PLANT LILIUM 'ORANGE FLASH'

[75] Inventor: Judith F. McRae, Boring, Oreg.

[73] Assignee: Mt. Hood Lilies, Inc., Sandy, Oreg.

[21] Appl. No.: 100,900

[22] Filed: Jul. 30, 1993

[51] Int. Cl.[5] ..... A01H 5/00

[52] U.S. Cl. ..... Plt./87.4

[58] Field of Search ..... Plt. 87.4

*Primary Examiner*—David T. Fox

[57] ABSTRACT

A new variety of hybrid lily plant bearing large upright-facing flowers of excellent form and long persistence, both on the plant and as cut-flowers. The flowers of the new hybrid are particularly characterized by their large size and substance and by their unusual orange flowers with a large white area in the center of each tepal. This combination is completely new in the Asiatic hybrid divisions of lilies suited to forcing and to mass commercial cultivation. The variety is highly resistant to fusarium disease and shows tolerance of virus. The bulbs may be precooled and forced for cut-flower production. The clone is vigorous and is a good grower and propagator.

1 Drawing Sheet

BACKGROUND OF THE INVENTION

My new variety of lily plant originated as a seedling which first flowered in Boring, Ore. in 1988. The breeding efforts had as their objective the production of deeply colored Asiatics with a very light to white area in the center of each tepal, suited to forcing into flower out of season, heretofore unknown in the lily breeding art.

I achieved the desired objective by intercrossing two unnamed orange Asiatic seedlings, each of which had a much lighter orange area in the center of each tepal. Both of the unnamed seedling parents were produced by me by pollinating an unusual albino-flowered Asiatic mutant seedling (also produced by me and never released commercially) with Lilium 'Sunkissed' (unpatented). Although unpatented, 'Sunkissed' was a popular garden lily during the 1970's. Two siblings from this cross had orange flowers with very lighly pigmented tepal tips, and these were intercrossed to produce 'Orange Flash'. Two other siblings of 'Orange Flash' showed its distinctive flower color pattern, but both had distorted flowers.

The flowers of my new lily are characterized by an upfacing to slightly outfacing orientation, large size, and deep orange coloration with a wide white area in the center of each tepal. It possesses unusually strong, stout stems. In addition, the clone possesses to a high degree desirable characteristics of hybrid vigor. The clone is a good grower and propagator, as observed as Boring, Ore.

My new variety of lily plant has been asexually reproduced by me and under my direction at Boring, Ore. Successive generations produced by natural propagation from bulblets, bulbils, by bulb scale propagation, and by tissue culturing from bulb scale explants have demonstrated that the novel and distinctive characteristics of my new variety are fixed and hold true under asexual propagation from generation to generation.

DESCRIPTION OF THE DRAWING

My new variety of lily plant is illustrated in the accompanying photographic drawing, which shows the open bloom in full color and illustrates the flower form, the tepal arrangement, and in particular the novel and distinctive color pattern of its orange flowers with a pure white area in the center of each tepal.

DESCRIPTION OF THE NEW VARIETY

The following is a detailed description of my new variety of Asiatic hybrid lily, with nomenclature according to the *International Lily Register* (Royal Horticultural Society of London, Second Edition, 1969), and with color designations according to the Colour Chart of The Royal Horticultural Society, published by the Society in 1966.

The Plant

Origin: Seedling.

Seed parent: Unnamed seedling.

Pollen parent: Unnamed seedling.

Commercial classification: Hybrid Lilium clone.

Horticultural classification: Division IA, Upfacing Asiatic hybrid lily, according to the Horticultural Classification of Lilies, Royal Horticultural Society of London.

Form: Single stem, erect and stately.

Height: 70 to 125 cm from bulbs 14 to 18 cm in circumference, provided their light levels are adequate; low light levels may cause "stretching."

Growth: Vigorous and upright.

Foliage quantity: Abundant.

Size of leaf: 10 to 15 cm long×0.75 to 2 cm wide.

Shape of leaf: Lanceolate (pointed).

Texture: Leathery and glossy.

Color: Medium to light green, lighter on lower side.

Bulb size: Any size, ranging to 25 cm circumference commercially.

Bulb color: White, with flushes of pink or yellow after exposure to light.

The Bud

Form: Obtuse, ovoid, and long.

Size: 9 to 12 cm long and 10 to 14 cm in circumference just prior to opening.

Opening: Bud opens slowly, in response to morning light; this takes about one hour.

Color: RHS CC orange-red 33 D, with green midribs.

Peduncle: Averages 10–12 cm, but it may elongate if light levels are too low or if bulbs have been improperly stored prior to forcing. Color is deep green.

The Flower

Blooming habit: Annually in midseason; flowers once and profusely.

Size: Flowers are large-sized, averaging 14 to 18 cm in diameter, reflexing at the tips on the second day to 12–16 cm in diameter. The tepals are broad: outer tepals are 2.25 to 3 cm wide, and the inner tepals are 30 to 3.5 cm wide. The outer tepals are pointed.

Borne: In a single racemic inflorescence producing 4 to 10 flowers from a bulb 12 to 16 cm in circumference.

Shape: Form a broad, flat-faced bowl shape by the second day after opening, with the "bowl" 5–7 cm deep.

Tepalage: Typical of genus Lilium, with 6 imbricated tepals.

Tepal color: RHS CC orange-red 33 B/C, deepening to 34 C in the area parallel to the nectaries and extending 1 cm beyond the nectaries, with a pure white area 0.5–2 cm wide extending from that point along the midrib of each tepal towards the apex. The width of the white area varies from flower to flower but is always wider at the base and narrowest near the apex. The nectaries vary from soft green to pale ivory under low light conditions, but when grown in bright light are soft orange. They are pubescent, with short white hairs noticeable when the flowers are completely open.

Tepal spotting: Tepals are lightly spotted with medium-sized dark magenta-black spots in the orange-colored area at the base of each tepal.

Tepal longevity: Tepals stay on stems about three weeks.

Pedicel length: Average 8 to 12 cm long.

Pedicel color: Dark, glossy plum (heavy anthocyanin over dark green).

Pedicel form: Sturdy and slightly ascending.

Color changes: Flowers become slightly lighter as the flowers age. Low light levels and extreme heat may cause the white area to decrease slightly.

Appearance: Flower is shiny.

Disease resistance: The flower and plant are resistant to disease; in particular, they are resistant to Fusarium bulb rot and Botrytis blight.

Fragrance: None.

Lasting quality: The flower is long lasting, both on the plant and as a cut-flower.

The Reproductive Organs

Stamens: Arrangement typical of genus Lilium. Six stamens with very light orange to white filaments 8 to 10 cm long.

Pollen and anthers (dehisced): RHS CC greyed red 178A to 182 A, may bleach to greyed orange 170 A under very hot conditions.

Pistil: One in number, 6 to 8 cm long, very light orange in color.

Stigma: RHS CC greyed purple 183 C/D, medium in size.

Characteristics of ovary: Characteristic of genus Lilium.

The Fruit

Fertility: The fruit bears fertile seed.

Shape: Ovoid.

Color at maturity: Soft brown, sometimes overlaid with soft plum.

My new variety of Asiatic hybrid lily most nearly resembles 'Charleston' in the pattern of its color distribution (with carotene pigments expressed at the tepal base and along the tepal margins, but absent in the midrib of each tepal), but it is orange rather than yellow. 'Sunkissed' has a similar but lighter orange color and shows a much paler area at the apex of each tepal under hot conditions, but this never shades into true white.

I claim:

1. A new and distinctive variety of Asiatic hybrid lily plant substantially as herein shown and described, characterized by its high resistance to disease; its tolerance of virus; its vigorous growth and rapid natural propagation; the excellence of its flower form, size, and substance; its versatility both as a garden plant and as a cut-flower produced from pre-cooled bulbs forced under glass out of season; and in particular by the unique color pattern of its orange flowers with their broad white area extending along the midrib of each tepal, a combination unique among Asiatic hybrid lilies suited to forcing and to mass commercial cultivation.

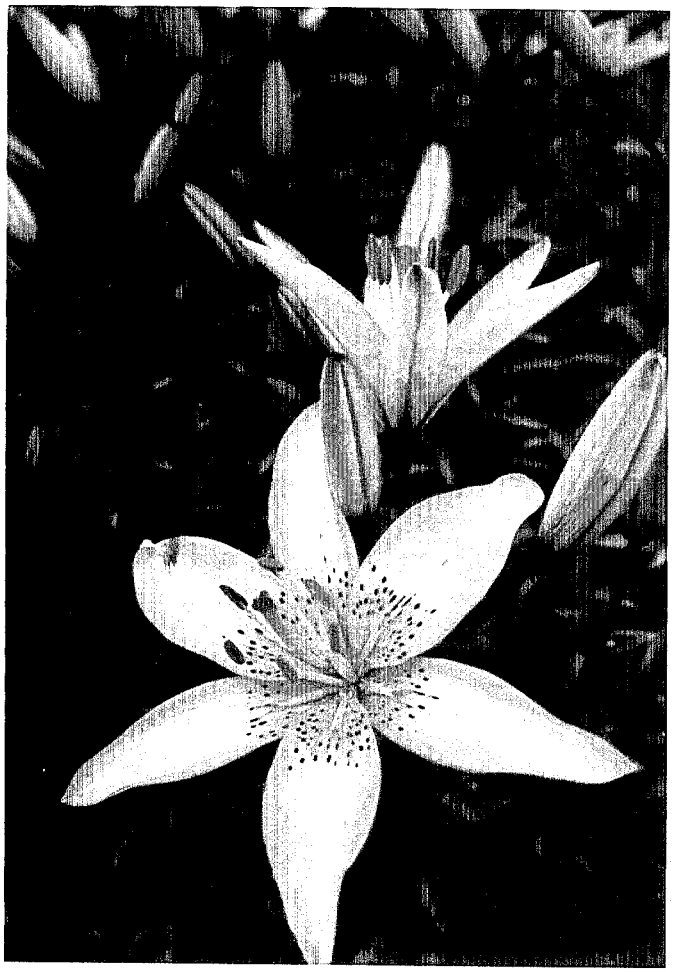

* * * * *